(12) United States Patent
Rosati (10) Patent No.: US 8,900,209 B2
(45) Date of Patent: Dec. 2, 2014

(54) METHOD AND APPARATUS FOR SUPPLYING GAS TO AN AREA

(75) Inventor: Coni F. Rosati, Carlsbad, CA (US)

(73) Assignee: Oxyband Technologies, Inc., Woodbury, MN (US)

(*) Notice: Subject to any disclaimer, the term of this patent is extended or adjusted under 35 U.S.C. 154(b) by 0 days.

(21) Appl. No.: 13/459,680

(22) Filed: Apr. 30, 2012

(65) Prior Publication Data

US 2013/0112077 A1    May 9, 2013

Related U.S. Application Data

(60) Continuation of application No. 11/485,513, filed on Jul. 11, 2006, now Pat. No. 8,166,731, which is a division of application No. 11/356,929, filed on Feb. 16, 2006, which is a continuation-in-part of application No. 10/781,965, filed on Feb. 18, 2004, now Pat. No. 7,014,630.

(60) Provisional application No. 60/479,745, filed on Jun. 18, 2003, provisional application No. 60/654,037, filed on Feb. 17, 2005, provisional application No. 60/662,019, filed on Mar. 14, 2005, provisional application No. 60/711,796, filed on Aug. 26, 2005.

(51) Int. Cl.
*A61F 13/00* (2006.01)
*A61F 9/00* (2006.01)
(Continued)

(52) U.S. Cl.
CPC .. *A61F 13/00051* (2013.01); *A61M 2202/0208* (2013.01); *A61M 35/006* (2013.01);
(Continued)

(58) Field of Classification Search
CPC ............ A61M 35/006; A61M 1/0088; A61M 2202/0208; A61F 13/02; A61F 13/0206; A61F 13/0213; A61F 13/0216; A61F 13/0223; A61F 13/0226; A61F 13/023; A61F 13/0233; A61F 13/0236; A61F 13/0243; A61F 13/0256; A61F 13/0266; A61F 2013/0017; A61F 2013/00174; A61F 2013/00246; A61F 2013/00255; A61F 2013/0285; A61F 2013/0034; A61F 2013/00344; A61F 2013/00872; A61F 2013/0097; A61F 13/00051; A61F 9/0008; A61H 2033/143; A61H 33/14; B65D 81/2069; A61L 2/20; A61L 2/202; B65B 31/02; B65B 31/024; B65B 31/04
USPC ......... 604/305, 304, 306, 307, 308, 540, 541, 604/543, 23, 24, 26
See application file for complete search history.

(56) References Cited

U.S. PATENT DOCUMENTS 4,224,941 A * 9/1980 Stivala ........................... 604/23
4,969,869 A * 11/1990 Burgin et al. .................. 604/23
(Continued)

OTHER PUBLICATIONS

Online dictionary entry for "generate." http://www.thefreedictionary.com/generate. Accessed Jul. 5, 2013.*

*Primary Examiner* — Adam Marcetich
(74) *Attorney, Agent, or Firm* — Donald R. Bays; Central Coast Patent Agency, Inc.

(57) ABSTRACT

Embodiments of the present invention are directed to various designs and packaging methods for a gas delivery device and materials for supplying one or more predetermined gases to a target area as well as to application specific opthamological embodiments. With regard to the gas delivery device, the device may include a reservoir, a gas diffusion portion for communicating gas from the reservoir and one or more predetermined gases at concentrations greater than atmospheric contained within the reservoir, wherein the device does not generate gas and may be packaged prior to use with the one or more predetermined gases.

11 Claims, 10 Drawing Sheets

(51) Int. Cl.

| | | |
|---|---|---|
| *A61F 13/40* | (2006.01) | |
| *A61F 13/02* | (2006.01) | |
| *A61M 35/00* | (2006.01) | |
| *B65B 31/00* | (2006.01) | |
| *B65D 81/20* | (2006.01) | |
| *A61H 33/14* | (2006.01) | |
| *A61H 35/00* | (2006.01) | |
| *B65B 25/00* | (2006.01) | |

(52) U.S. Cl.
CPC ............ *A61F 13/0206* (2013.01); *A61F 13/02* (2013.01); *A61F 2013/00174* (2013.01); *A61F 2013/0017* (2013.01); *A61H 33/14* (2013.01); *A61H 35/00* (2013.01); *A61H 2033/143* (2013.01); *A61M 35/00* (2013.01); *B65B 25/008* (2013.01); *B65B 31/00* (2013.01); *B65D 81/2069* (2013.01); *A61F 9/0008* (2013.01)

USPC .......... 604/305; 604/306; 604/304; 604/308; 604/23; 604/24

(56) References Cited

U.S. PATENT DOCUMENTS

| | | | | |
|---|---|---|---|---|
| 5,154,697 | A * | 10/1992 | Loori | 604/23 |
| 5,374,243 | A * | 12/1994 | Whalen et al. | 604/23 |
| 5,614,212 | A * | 3/1997 | D'Angelo et al. | 424/449 |
| 5,662,625 | A * | 9/1997 | Westwood | 604/305 |
| 5,788,682 | A * | 8/1998 | Maget | 604/290 |
| 5,792,090 | A * | 8/1998 | Ladin | 602/48 |
| 6,000,403 | A * | 12/1999 | Cantwell | 128/888 |
| 6,073,759 | A * | 6/2000 | Lamborne et al. | 206/213.1 |
| 7,014,630 | B2 * | 3/2006 | Rosati | 604/304 |
| 7,263,814 | B2 * | 9/2007 | Rosati | 53/432 |
| 7,762,045 | B2 * | 7/2010 | Rosati | 53/403 |
| 8,166,731 | B2 * | 5/2012 | Rosati | 53/432 |
| 2002/0155027 | A1 * | 10/2002 | Gutman | 422/29 |

* cited by examiner

METHOD AND APPARATUS FOR SUPPLYING GAS TO AN AREA

RELATED APPLICATIONS

This application is a continuation of U.S. application Ser. No. 11/485,513, filed Jul. 11, 2006, which is a divisional application of U.S. application Ser. No. 11/356,929, filed Feb. 16, 2006, which is a continuation-in-part (CIP) application of U.S. published application, publication no. 2004/0260253 A1 (U.S. application Ser. No. 10/781,965) filed Feb. 18, 2004, entitled, "Tissue Dressing Having Gas Reservoir", which issued as U.S. Pat No. 7,014,630 on Mar. 21, 2006, which claims priority to U.S. Application Ser. No. 60/479,745, filed on Jun. 18, 2003.

U.S. application Ser. No. 11/356,929 also claims priority to U.S. provisional patent application Nos. 60/654,037, filed Feb. 17, 2005, entitle, "Packaging Products with a Gas and Products For Releasing the Gas Upon Use"; 60/662,019, filed Mar. 14, 2005, entitled, "Methods and Apparatuses for Packaging Products with a Gas"; and 60/711,796, filed Aug. 26, 2005, entitled, "Methods and Applications related to Oxygen Charged Tissue Dressing".

All of the foregoing disclosures are herein incorporated by reference in their entirety.

FIELD OF THE INVENTION

The present invention relates generally to devices (which may also be referred to as apparatuses, systems or products) for supplying/delivering one or more particular gases to a desired area, use of such gas supplying devices, and systems and methods for packaging such devices with one or more particular gases.

BACKGROUND OF THE INVENTION

This application includes citations to various publications, patent applications and issued patents, each of which is herein incorporated by reference in its entirety.

Oxygen's role in wound healing has been intensively studied. In that regard, the background section of published parent no. 2004/0260253 A1 (the '253 publication) presents a discussion of wound recovery with respect to oxygen supply and further teaches how a simple dressing can supply oxygen to a wound area at high concentrations without the need for producing oxygen chemically, electrochemically or from a tethered source. In addition, devices disclosed in the '253 publication allow for the delivery of other gases at predetermined gas ratios to tissues and other target areas. This simple means to manipulate and optimize local environments can be used alone or in combination with other materials and/or devices to create additive and sometimes synergistic outcomes (e.g., heat, electrical stimulation, growth factors, and nutrients), or using oxygen in combination with antibiotics topically to enhance antimicrobial effectiveness.

SUMMARY OF THE INVENTION

In view of oxygen's benefits to speed healing and the reduction of infection and pain for wounds, whether on the surface or interior of tissues, embodiments of the present invention include further means to supply oxygen, as well as other gases and gas-ratios, to a wound on a continuous and ambulatory basis, as well as other gases and gas ratios.

Beyond wounds, there are benefits to manipulating local environments with one or more predetermined gases. Local environments may be manipulated in order to accelerate growth of cells, preserve or extend the life of cells and/or tissues, to retard/maintain/accelerate biochemical reactions, to sustain/accelerate/suppress chemical reactions, and the prevention of corrosion. For example, attaching a gas emitting pouch to the inside lid of a petri dish to preserve cells. In some cases, oxygen may be released to manage metabolic processes, in other cases carbon dioxide could be released (or a ratio of oxygen to carbon dioxide, etc.). In still other cases, gas emitting devices may be used as biocides to inhibit the growth of or kill organisms—like the use of oxygen to kill anaerobic organisms or chlorine dioxide to kill bacteria, fungi and algae. Some of the embodiments of the present invention may include further means to supply gases and gas ratios to a local area such as cells, tissues, containers, surfaces and non-biological systems.

Accordingly, some embodiments of the invention include methods and devices which saturate and/or super-saturate, absorb or adsorb, or take up gases (hereinafter referred to as "gas infusion", "gas infusing" or "gas infused") into a device with a single gas (e.g., oxygen, carbon dioxide), or, in some embodiments, infused with a plurality of gases. Such a device may become infused with a subset of the gas(es) inside a sealed package by diffusing passively from predetermined gas(es) stored in the package to the device also stored in the package. This method can also be used to preserve the gas levels precharged in or on a device by packaging the device with gases that will maintain the predetermined gas levels in the device. Upon opening the sealed package, the device may be used to deliver the infused gas(es) to a target area. For example, the product may be a medical related product such as a topical dressing or implant infused with oxygen (for example) which can then deliver oxygen to a target area of the body. An eye patch or dressing, for example, could be applied to oxygenate the eye for purposes such as to enhance healing or provide oxygen as a nutrient.

Other examples of gas infused and gas emitting health care products may include (but not limited to): injectables, topical agents, contact lenses, implantable lenses, ingested devices, inhaled materials, face masks, socks, boots, insoles, gloves, sutures, pills, dermal fillers, wound healing gels, gum and the like. These products may also contain other therapeutic materials in addition to the infused gas, or may contain agents/ingredients to facilitate the uptake and release of the gas(es). Such embodiments may include a pre-packaged gas-infused gel and/or foam, for supplying one or more predetermined gases to a target environment.

Accordingly, some of the embodiments of the present invention may include devices that are capable of providing one or more predetermined gases to a target area ("a gas delivery device"). Such embodiments may include one or more gas reservoirs which may be formed between similar or dissimilar layers of material or are enveloped within a continuous layer of material.

In one embodiment, a multi-layer wound device ("dressing") comes pre-filled with a predetermined amount of oxygen between the layers. The top layer is a barrier film that holds the oxygen over the wound, while the bottom layer is a gas permeable membrane, which may be designed to have a specific rate of gas transfer. The bottom layer is typically placed over the wound in some applications, like conventional wound dressings, and can be manufactured with a similar size, weight and feel of conventional dressings or transdermal patches. The top or barrier layer retains the oxygen in the vicinity of the wound, while the bottom or permeable (or porous) layer allows the oxygen to diffuse into the wound at a rate proportional to the gradient (for example), until the wound is saturated. The dressing acts like a local abundant oxygen supply to be used as needed. The geometry can be adjusted from simple rectangular or circular packets to more complicated geometries such as socks, gloves, masks and eye patches for wounds located on the body where there are more contours, bends, crevasses and protuberances.

Such a dressing according to some of the embodiments may be provided to a user in a sealed package, and may be pre-filled with a predetermined amount of one or more gases. In one embodiment, the package is filled with a predetermined amount of one or more gases (e.g., substantially pure oxygen—preferably 100% oxygen) which may be accomplished using, for example, controlled atmospheric packaging (CAP). When the gases in the reservoir are different in type or concentration than gases sealed in the package, gases diffuse through the permeable portion of the dressing until reaching equilibrium when the gases and gas concentrations are the same within the package and the reservoir. This passive diffusion until equilibrium is a simple method to infuse or charge the reservoir with the desired gas levels.

Another embodiment of the invention may include a gas delivery device for supplying one or more predetermined gases to a target environment, where the device may include a reservoir, a gas diffusion portion for communicating gas from the reservoir and include one or more predetermined gases. The device does not generate gas and may be packaged prior to use with the one or more predetermined gases. As in the previous embodiment, when the gases in the reservoir are different in type or concentration than the gases sealed in the package, gases may diffuse through the permeable portion of the device until reaching equilibrium, when the gases and gas concentrations are the same within the package and the reservoir.

In another embodiment of the invention, a gas delivery device for supplying one or more predetermined gases to a target environment is provided, similar to the above-noted embodiment, and also including a preset volume of one or more predetermined gases.

Another embodiment of the invention includes a gas delivery device which may be in the form of a contact lens for supplying one or more predetermined gases like oxygen (for example) to a target environment such as the cornea, retina or eye. Oxygen is stored either between layers as gas, or as an oxygen saturated or oxygen carrying solution between the layers and/or absorbed reversibly in a lens material that lacks a reservoir between layers.

Other embodiments of the invention include devices having one or more reservoirs (or designated areas of the device) pre-filled with one or more predetermined gases (e.g., oxygen) according to a predetermined amount corresponding to levels other than that contained in the ambient atmosphere. The reservoir may be formed between layers of material for such devices, or enveloped within a continuous layer of material, or the material itself may act as a reservoir as it contains gas either in its micro or macro cavities (such as foam or gel) or by reversibly adsorbing or absorbing gas molecules.

The gas infused products according to some embodiments fill multiple micro-reservoirs with designated gas(es) by coming to equilibrium with the gas for infusion during packaging or in the package. In some embodiments, the gas permeates through the product (e.g., a solid, semi-solid, fluid or semi-fluid), diffusing therein (i.e., absorbed/adsorbed) by coming to equilibrium with the gas for infusion in the package. In other embodiments, gas infusion of products may be accomplished in the package at a temperature and/or pressure greater than atmosphere in order to hasten or increase the rate or levels of taken up by the product.

In another embodiment of the invention, a method of packaging a gas delivery device is described that creates a flatter package as one particular advantage. The gas delivery device may comprise a reservoir including one or more predetermined gases, and a gas diffusion portion for communicating the one or more predetermined gases from the reservoir. The gas delivery device may be packaged with the one or more predetermined gases that may or may not be the same gas types or levels as contained in the reservoir. Such a packaging method may include placing the gas delivery device into a package, where the package capable of being substantially gas-impermeable when sealed, and the package may be filled with the one or more predetermined gases and sealed. Then, after a predetermined period of time has elapsed, pressure is applied to the outside of the package to release excess gas through a port or a puncture, and then resealed either by a self sealing design (self-sealing material included around the port or puncture) or via an external operation (such as heat sealing). In another embodiment, the port may allow gas to be removed without the need for pressure being applied externally to the package.

In the above-noted embodiment, after the pressure to the outside of the package is removed, the self-sealing material seals the puncture. Alternatively or in addition thereto, the excess one or more predetermined gases may be released through a valve, which may be a one-way valve. Such valves may release the excess one or more predetermined gases upon the pressure in the package reaching a predetermined level.

Further to the above-noted embodiment, immediately prior to removing the pressure applied to the outside of the package to release the excess one or more predetermined gases, the method may further include re-sealing the package (e.g., heat sealing).

Other embodiments of the invention may be directed to a contact lens case which may include a container holding at least one contact lens and also for optionally holding contact lens solution and one or more predetermined gases at concentrations greater than atmospheric included within the reservoir.

A related embodiment may include a contact lens oxygenation system which may include a container for holding a contact lens, an inlet for supplying a flow of oxygen to the container, a supply of oxygen capable of providing a flow of oxygen to the inlet and a one-way valved outlet for releasing excess pressure from the container.

A further related embodiment may include a method for oxygenating a contact lens which may include providing at least one contact lens container for holding at least one contact lens in a sealed state, positioning at least one contact lens inside the at least one contact lens container, providing oxygen to the inside of the at least one contact lens container in concentrations greater than atmospheric or ambient pressure. Providing oxygen may include establishing a flow of oxygen into the container. Moreover, the container may include a one-way valve such that upon the flow of oxygen being established excess pressure is released from within the container upon the pressure reaching a predetermined level.

These and other embodiments, objects and advantages of the system will become more apparent with reference to the following detailed description and attached figures.

BRIEF DESCRIPTION OF THE DRAWINGS

The accompanying drawings, which are incorporated in and constitute a part of this specification, illustrate one embodiment of the invention and, together with the description, explain one embodiment of the invention. In the drawings.

DETAILED DESCRIPTION

Figure 1:
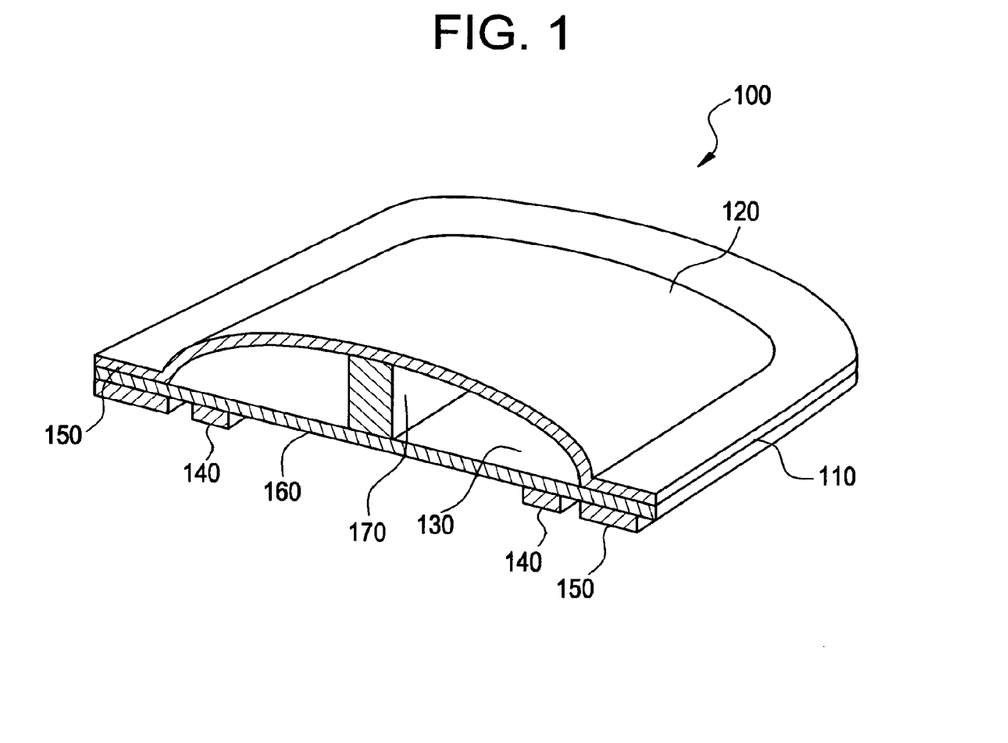
FIG. 1 illustrates one embodiment of a dressing system.

FIG. 1 illustrates an example of one embodiment of the invention of an apparatus for supplying one or more gases to a target area. With reference to use of such an embodiment on biological tissue, this embodiment may be referred to herein as a tissue dressing system 100 (also known as a gas-delivery device). The dressing system 100 is shown as an exemplary perspective cut-away view for clearer understanding. The dressing system 100 may be configured to contain one or more predetermined gases. While any one or more known gases (or volatiles) may be used, the gases included with the dressing system 100 may particularly include oxygen, carbon dioxide, nitrogen and nitric oxide, and combinations thereof. The dressing system can also be used to supply gases to any target areas that would benefit from a locally controlled gas supply such as containers in which it is desired to retard, accelerate, or maintain biochemical reactions, sustain, accelerate, and/or suppress chemical reactions, corrosion, or inhibit the growth or kill organisms.

The dressing system 100 may include a seal 110, an external barrier (or top layer) 120, a reservoir 130, an absorbent ring 140, an adhesive backing 150, a permeable film (or bottom layer) 160, and a compliant porous insert 170. As shown, the reservoir may be formed between the upper and lower layers (e.g., being hermetically sealed around the perimeter), but may also be a separate element to the dressing system, or contained within a continuous layer. To that end, in one embodiment, the seal 110 is configured to bond the external barrier 120 and the permeable film 160 together such that the reservoir 130 is formed.

The external barrier 120 is preferably selected to be non-permeable to gases. For example, the external barrier 120 may be constructed of metallized polyester, ceramic coated polyester, polyvinylidene chloride laminates such as Saranex®, EVOH laminates such as Oxyshield®, or polyamide laminates such as Capran®. In one embodiment, the external barrier 120 may be configured to conduct heat or electrical stimulation from an external source to the user. For example, polyethylene or another infrared transmittable material may be utilized as the external barrier 120.

The permeable film 160 is preferably configured to be permeable to gases. For example, the permeable film 160 may be constructed of polyurethane, silicone, polyvinylchloride, polyolefins, and the like, preferably ethylene vinyl alcohol (EVA) or EVA/polyethylene.

The reservoir 130 is configured to store a gas while the dressing system 100 is worn by a user. In one embodiment, the stored gas within the reservoir 130 is controllably released to the user through the permeable film 160. The amount of gas released to the user while wearing the dressing system 100 may vary according to the concentration of the gas contained within the reservoir 130 and the material used as the permeable film 160. Other factors such as temperature and atmospheric pressure may also affect the amount of gas released to the user.

The absorbent ring 140 may be located adjacent to the permeable film 160 and may be configured to wick away moisture from the user. In addition, the adhesive backing 150 is configured to adhere the dressing system 100 to the user. Further, the adhesive backing 150 may also be utilized to prevent the gas that is delivered through the permeable film 160 to the user from escaping. In one embodiment, the adhesive backing 150 may cover the perimeter of the dressing system 100. In another embodiment, the adhesive backing may cover the entire dressing system 100 and may be integrated with the permeable film 160. In another embodiment the adhesive may be on the opposite side attaching the top film, for example, to the inside lid surface of a container allowing the gas to transfer through the bottom film over the entire volume of the closed container such as a Petri dish.

Examples of the types of adhesive that may be used in the present invention are described in U.S. Pat. Nos. 6,284,941 and 5,308,887. In one embodiment, the adhesive backing may be comprised of adhesive used in commercially available adhesive bandages. In another embodiment, the adhesive backing may be comprised of a gel adhesive. The gel adhesive may be comprised of a hydrogel. The gel adhesive may also be reusable, such that the dressing system could be removed from the user and replaced more than once. Examples of gels that may be used are described in U.S. Pat. Nos. 4,839,345, 5,354,790 and 5,583,114.

The compliant porous insert 170 is configured to prevent gas debt in areas caused by pressing the external barrier 120 directly on to the permeable film 160. In one embodiment, the compliant porous insert 170 placed within the reservoir 130 and between the external barrier 120 and the permeable film 160.

The proportions of gas-delivery device according to embodiments of the present invention (e.g., dressing system 100) may be influenced by the diffusion rates of the relevant gases through the permeable portion (e.g., film 160), the target gas concentration range (e.g., on the user), and the length of time the gas delivery device is used (e.g., the length of time the dressing system 100 may be worn). If the gas-delivery device includes a seal, then the proportions of the device may be also influenced by the seal integrity between the dressing system 100 and the user.

Some embodiments of the present invention for supplying one or more gases to a target area may also include devices having a continuous layer of gas permeable/porous material which, in some aspects, envelops the one or more predetermined gases. As shown in FIGS. 7A-7E, such continuous layer geometries may include a balloon, a tube, an O-ring, a pouch, a teabag/sachet, a curved material (e.g., a contact lens) or a combination of the foregoing. Materials used for these various embodiments may depend on the application—biocompatible or bioerodible materials can be used for implantable sustained release devices It is worth noting that some embodiments of the present invention include gas infused devices having controlled and/or customized gas diffusion rates. Specifically, such embodiments may include pre-determined diffusion rates which may be determined by controlling the type of membrane being used, the size and/or amount of pores and/or erosion areas.

In some embodiments, in addition to providing gas to a target area, the gas-delivery device may be configured to deliver biologically beneficial agents such as drugs, minerals, nutrition, amino acids, pH modifiers, anti-microbials (e.g., antibacterials and antifungals), growth factors, and enzymes to the user. In one embodiment, integrating the delivery systems of the gas with the beneficial agent additives may lead to synergistic effects that are not achieved by just the gas or the beneficial agent additives alone. In one embodiment, these biologically beneficial agents may be delivered as microencapsulated agents incorporated in the adhesive backing 150. In another embodiment, the microencapsulated agents may be available in a gel matrix in the dressing cavity 180, accessible to the wound through pores or perforations, or using conventional transdermal technologies.

In another embodiment, the dressing system as described herein may further comprise a septum, which is defined herein as any type of septum, valve, Luer-type fitting or any resealable opening through which one or more gases can be introduced into the dressing system, then resealed to prevent the one or more gases from escaping. The dressing system of this embodiment may be applied to the wound, then the one or more gases in the desired ratio may be introduced into the dressing system, e.g., with a syringe. The septum would also allow for refilling of the dressing system, if desired.

Figure 3:
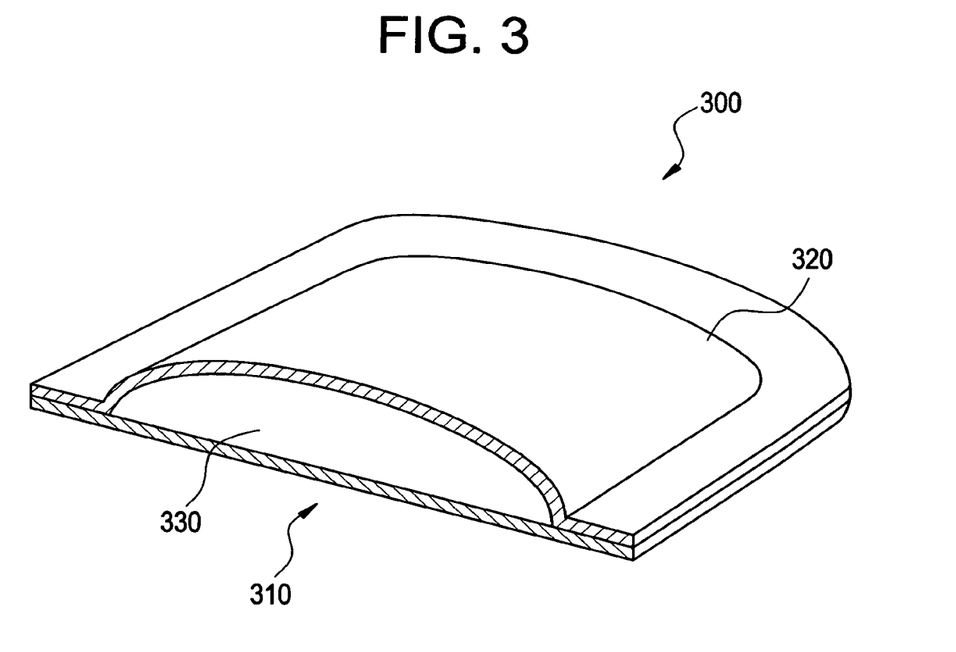
FIG. 3 illustrates one embodiment of a gas emitting pouch system.

FIG. 3 illustrates another embodiment according to the present invention—a gas emitting pouch system 300. The gas emitting pouch system 300 is shown as an exemplary perspective cut-away view to more clearly illustrate the invention. In one embodiment, the gas emitting pouch system 300 is configured to contain a gas that is dispensed to the local area surrounding the gas emitting pouch system 300. For example, the different gases contained within the gas emitting pouch system 300 may include but is not limited to oxygen, carbon dioxide, and/or nitrogen.

The gas emitting pouch system 300 may also include a first permeable film 310, a second permeable film 320, and a reservoir 330.

In one embodiment, the first permeable film 310 is coupled with the second permeable film 320 and forms the reservoir 330 for storing gas within the gas emitting pouch system 300. For example, the first and second permeable films 310 and 330 may be constructed of the same or different materials such as polyurethane, polyethylene, silicone films, polyvinylchloride, and the like.

The reservoir 330 is configured to store a gas while the gas emitting pouch system 300 is being used. In one embodiment, the stored gas within the reservoir 330 is controllably released to the area surrounding the gas emitting pouch system 300 through the first and second permeable films 310 and 320.

The amount and rate of gas released through the gas emitting pouch system 300 may vary according to the concentration gradients of the gas across the permeable films that comprise the walls of reservoir 330 and the materials used as the first and second permeable films 310 and 320. 310 and 320 can be the same or different materials. The amount and rate of release of gas can be different on the opposite sides, this can occur when 310 and 320 have different permeabilities. Other factors such as temperature, humidity and atmospheric pressure may also affect the amount of gas released.

The elements comprising the gas emitting pouch system 300 are shown for illustrative purposes only. Deletion or substitution of any shown elements does not depart from the spirit and scope of the invention. Similarly, the addition of new elements does not depart from the spirit and scope of the invention.

In one embodiment, the gas emitting pouch system 300 is configured prefilled with the desired gas concentrations and is stored within the packaging system 200 (FIG. 2) prior to releasing gas into the surrounding environment, also prefilled with the same gas concentrations as in the gas emitting pouch, in order to maintain the levels in the pouch. In another embodiment, the gas within the reservoir 330 within the gas emitting pouch system 300 comes to equilibrium within the packaging system 200 so that both the pouch and the package reach the target concentrations.

In one embodiment, the gas emitting pouch system 300 is configured to be placed in an environment where the gas stored within the reservoir 330 is released steadily into the surrounding environment, as the gradient doesn't change appreciably. In another embodiment, the release rate of gas from the reservoir 330 into the surrounding environment slows as the surrounding environment becomes saturated with the gas. Subsequent to the saturation, the gas emitting pouch system 300 acts as a gas reservoir; as gas is dissipated from the surrounding environment, there is a local supply of gas within the reservoir 330 to be provided to the surrounding environment, governed by the transfer rate across the permeable film.

The gas emitting pouch 300 has many applications which may include non-medical applications such as applying the gas emitting pouch 300 to effect environments in containers for any purpose such as lab experiments, food preservation, to accelerate degradation, to prevent corrosion, and the like.

Figure 6:
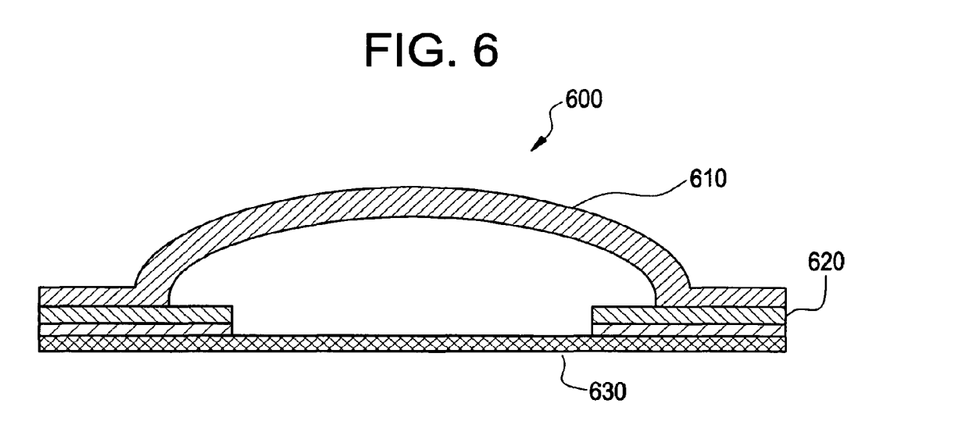
FIG. 6 illustrates one embodiment of a pouch system.
Figure 7A:
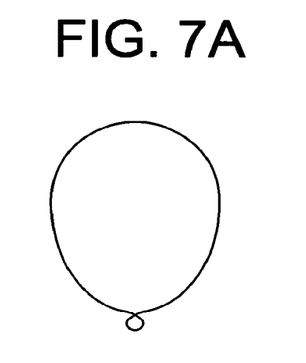
FIG. 7A is an illustration of a material for use in a continuous-layer, gas-delivery device comprising a balloon.
Figure 7B:
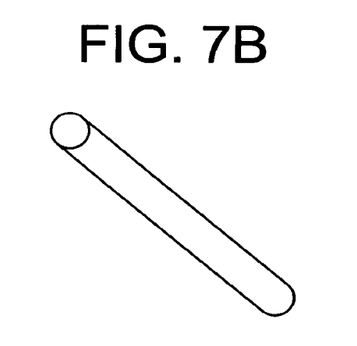
FIG. 7B is an illustration of a material for use in a continuous-layer, gas-delivery device comprising a tube.
Figure 7C:
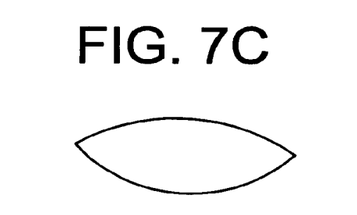
FIG. 7C is an illustrations of a material for use in a continuous-layer, gas-delivery device comprising a pouch.
Figure 7D:
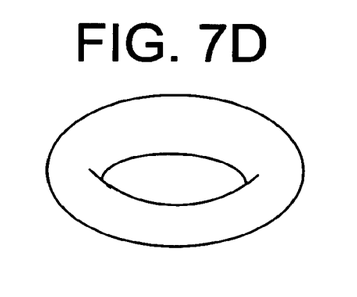
FIG. 7D is an illustration of a material for use in a continuous-layer, gas-delivery device comprising an O-ring.
Figure 8:
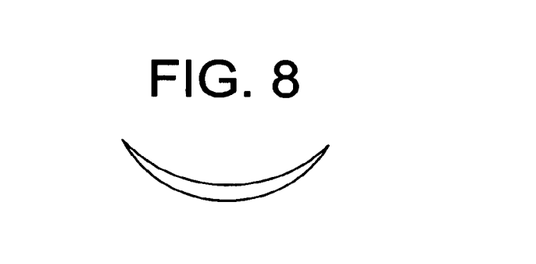
FIG. 8 is an illustration of a gas-delivery device according to an embodiment of the invention comprising a contact lens.

FIG. 6 illustrates another example of a pouch system. The pouch system 600 is configured to emit gas into a local environment, similar to the gas emitting pouch system 300. The pouch system 600 includes a first layer 610 and a second layer 630. The first layer 610 and the second layer 630 may be permeable to gases. In one embodiment, the first layer 610 and the second layer 630 are bonded through an intermediate layer 620. The intermediate layer 620 provides the pouch system 600 a more resilient and durable seal between the first layer 610 and the second layer 630 by diverting the load so that more robust shear force is applied to a higher bond strength seal rather than strictly a design that puts all the internal pressure and load on a peel strength surface. By adding the intermediate layer 620 with a narrower diameter than the first layer 610, the seal between the first layer 610 and the second layer 630 is reinforced.

Packaging

One method of achieving the specified oxygen concentration in the reservoir 130 and to create the controlled atmospheric packaging is to (1) assemble dressing, sealing the reservoir with normal atmospheric conditions (about 21% oxygen); (2) place the dressing in a package (e.g., a metallized film package); (3) flush the package with substantially pure oxygen; and (4) sealing the package. In storage, the gas in the reservoir 130 will come to equilibrium with the gas in the package via the permeable film 160. When the package is received by the customer and opened, the gas in the reservoir will achieve about 95-98% oxygen. The materials and dimensions used are determined by taking into account these objectives. The final concentration in the reservoir depends upon the volume and ratios of gases. For example, a dressing containing about 10 cc of air in the reservoir placed in a package which is filled with about 200 cc oxygen will equilibrate at a final oxygen concentration of approximately 96%

$$\frac{202 \text{ cc oxygen}}{210 \text{ total cc gas}} = 96\%$$

Figure 2:
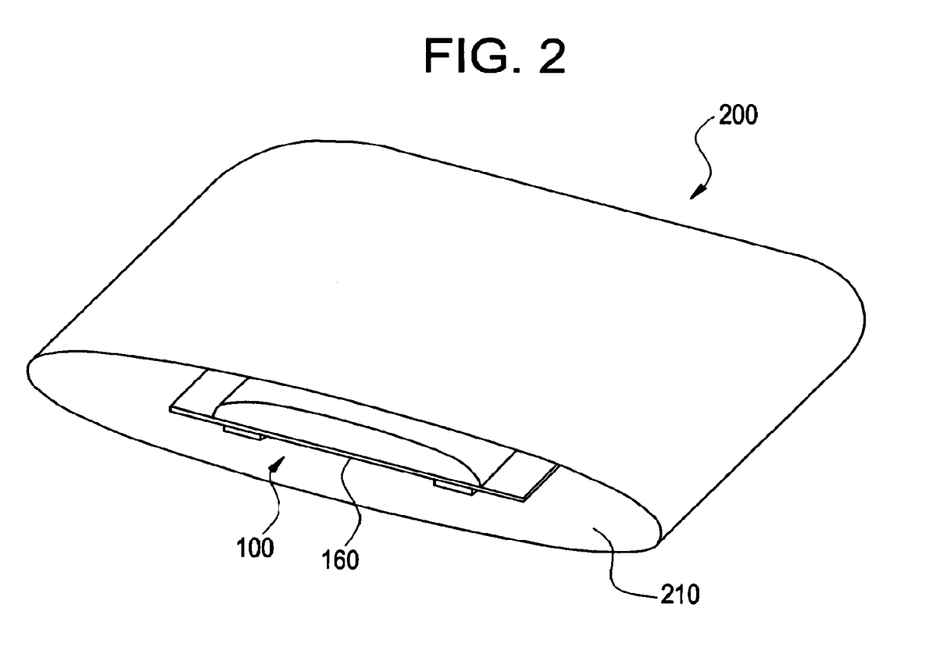
FIG. 2 illustrates one embodiment of a packaging system.

FIG. 2 illustrates an exemplary packaging system 200. The packaging system 200 is shown as an exemplary perspective cut-away view to more clearly illustrate the invention. In one embodiment, the packaging system 200 is configured to contain a gas within an enclosed container 210, which is within the packaging system. For example, the different gases contained within the dressing system 100 may include but is not limited to oxygen, carbon dioxide, nitrogen, and/or nitric oxide.

The enclosed container 210 may also be configured to hold the dressing system 100 as shown and described corresponding to FIG. 1. Once the enclosed container 210 is sealed, the enclosed container is substantially impermeable; the gas within the enclosed container 210 substantially remains within the enclosed container 210. Further, the enclosed container 210 utilizes controlled atmospheric packaging (CAP) to maintain the environment within the enclosed container 210. In one embodiment, CAP is a package with high barrier properties that contains the desired ratio of gases to preserve the internal environment. The gas within the enclosed container 210 may permeate the dressing system 100 through the permeable film 160.

In still other embodiments, a hole may be created in the dressing system (preferably on one side of the dressing, and preferably on the permeable side of the dressing), and the dressing placed in the package. The package is then evacuated which also evacuates the reservoir. The package is then filled with the one or more desired gases (e.g., oxygen) and sealed. Thereafter, the reservoir in the dressing fills with the gases contained in the package. The time it takes for the oxygen to enter the reservoir may be between less than a minute to several hours, and more preferably between about several minutes and several hours. It suffices to say, by the time the packaged dressing is sold, the reservoir contains sufficient amount of the packaged gases to supply a wound or other use. The hole in the dressing is sized so that upon opening of the package and removal/use of the dressing, a negligible amount of oxygen is released from the reservoir prior to application to the intended target area.

In some embodiments, to achieve desired gas concentration levels, CAP gas amounts in the package are sufficiently high so as to create a bulky package. For example, packaging for a wound dressing may be inflated with at least oxygen gas, causing the package to expand such that the package is bulky and much larger than the wound dressing. After a period of time sufficient enough to allow the oxygen to penetrate the dressing the remaining gas or a portion of the gas may be removed from the package. This allows the final package to be smaller and thus, shipped and distributed more easily.

The packaging system 200 may be utilized to store the dressing system 100 without degrading the gas stored within the reservoir 130 within the dressing system 100 when the gas within the reservoir 130 and the gas within the enclosed container 210 are the same.

The packaging system 200 may be utilized to change the concentrations of gases in the dressing system 100. The gas constituents stored within the enclosed container 210, diffuse into the dressing system 100 when the concentration of the gas within the container 210 is higher in concentration compared to the gas within the dressing system 100. Similarly, the gas constituents stored within the dressing system 100, diffuse into the container 210 when the concentration of the gas within the container 210 is lower in concentration compared to the gas within the dressing system 100. The gases may diffuse through the permeable film 160 until the constituents reach equilibrium, the same concentrations on both sides of the permeable film. In other embodiments, gas infusion may be accomplished in a barrier package at a temperature and/or pressure greater than atmosphere in order to hasten or increase the levels of taken up by a device.

Another embodiment of the packaging system comprises any of the packaging systems described herein and further comprises a septum, which as defined herein may be a septum, a valve, Luer lock or any resealable opening, through which one or more gases can be introduced into the packaging system, then resealed to prevent gases from escaping. The packaging system may be charged with the one or more gases in the desired ratio on site (e.g., hospital, doctor's office).

Figure 4:
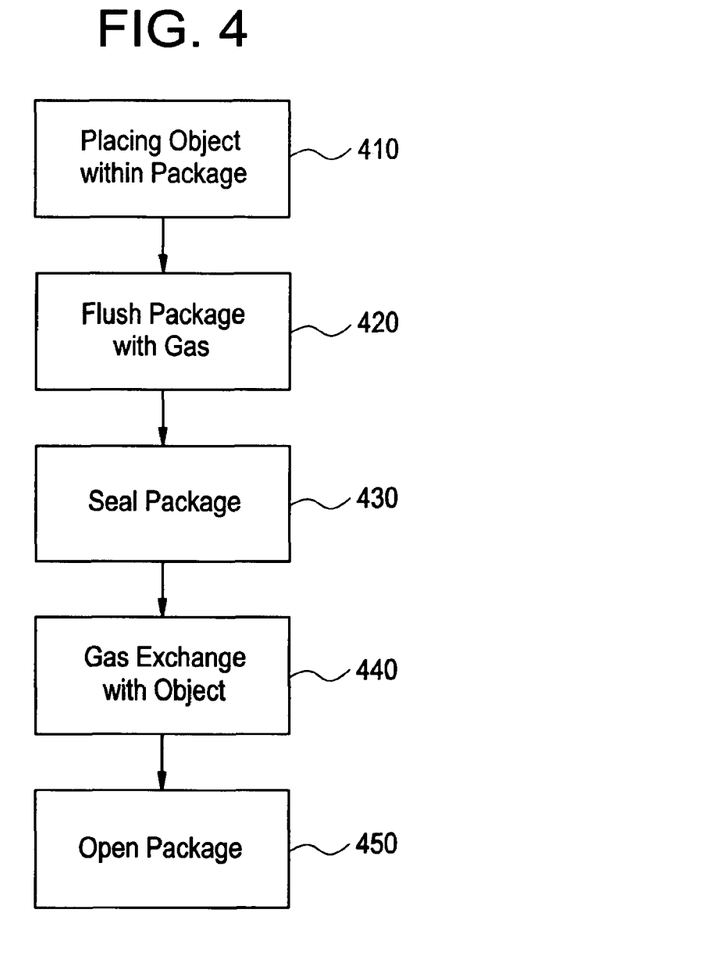
FIG. 4 illustrates a flow diagram for utilizing a packaging system according to one embodiment of the invention.

The flow diagram in FIG. 4 illustrates an exemplary process of utilizing the packaging system 200 according to one embodiment.

In Block 410, a gas-retaining object is placed within the packaging system 200. In one embodiment, the gas-retaining object is the dressing system 100. In another embodiment, the gas-retaining object is gas emitting pouch system 300. In yet another embodiment, the gas-retaining object may be any item that is configured to retain and controllably release a gas from the object.

In Block 420, the packaging system 200 is flushed with a gas. In one embodiment, the packaging system 200 is flushed with the same gas contained with the gas-retaining object. For example, the dressing system 100 may be pre-filled with oxygen and placed within the packaging system. By flushing the packaging system 200 with oxygen, the packaging system 200 ensures that the dressing system 100 retains the pre-filled oxygen content.

In another embodiment, the packaging system 200 is flushed with a different gas than the gas contained with the gas-retaining object. For example, the dressing system 100 may contain air that contains other gases in addition to oxygen and may be placed within the packaging system 200. By flushing the packaging system 200 with pure oxygen, the packaging system 200 diffuses the dressing system 100 with additional oxygen until the gas within the packaging system 200 and the gas within the dressing system 100 have reached an equilibrium.

In Block 430, the packaging system 200 is sealed after placing the gas-retaining object within the packaging system 200 and flushing the packaging system 200 with a gas.

In Block 440, if the gas within the gas retaining device and the gas within the packaging system 200 differ, then an exchange of gas occurs until an equilibrium is achieved. For example, by using the above example describing a dressing system 100 that contains air which is sealed within the packaging system 200 flushed with pure oxygen, the oxygen diffuses into within the dressing system 100, while nitrogen diffuses out of the dressing system 100 into the package 200 until an equilibrium is achieved between the gas within the dressing system 100 and the packaging system 200. In this embodiment, the gas may be exchanged through the permeable film 160 (FIG. 1).

In Block 450, the packaging system 200 may be opened to remove the gas-retaining object. The packaging system 200 may be utilized to store the gas-retaining object without degrading the gas within the gas-retaining object. In another embodiment, the packaging system 200 may be utilized to infuse the gas-retaining object with a gas.

Figure 9A:
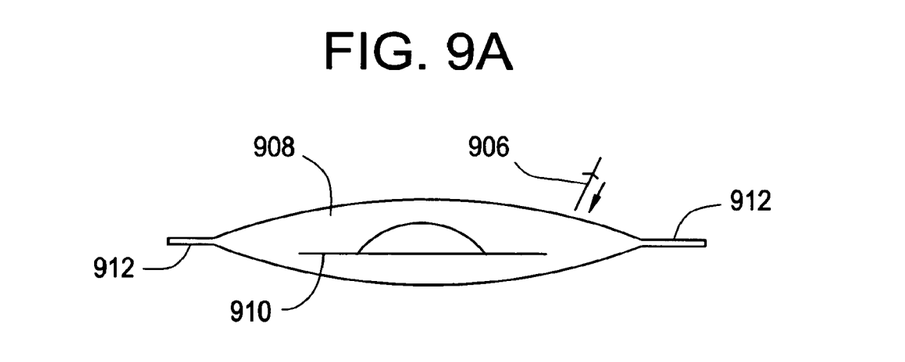
FIG. 9A is a first cross-sectional view of a packaging system for packaging a gas-delivery device according to an embodiment of the present invention.
Figure 9B:
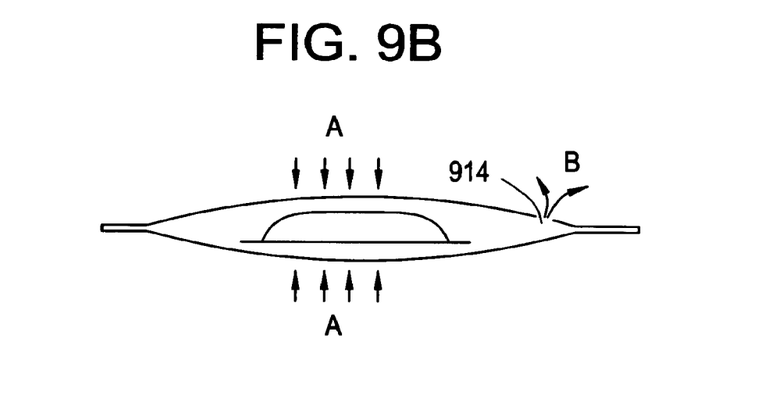
FIG. 9B is a second cross-sectional view of a packaging system for packaging a gas-delivery device according to an embodiment of the present invention.
Figure 9C:
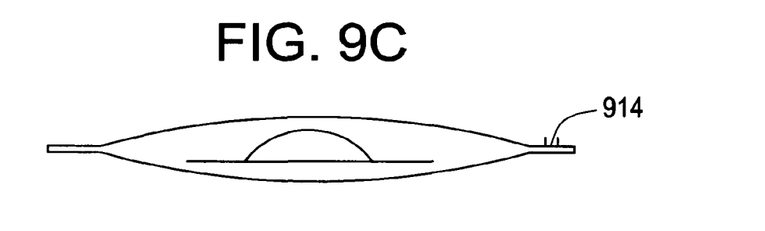
FIG. 9C is a third cross-sectional view of a packaging system for packaging a gas-delivery device according to an embodiment of the present invention.
Figure 9D:
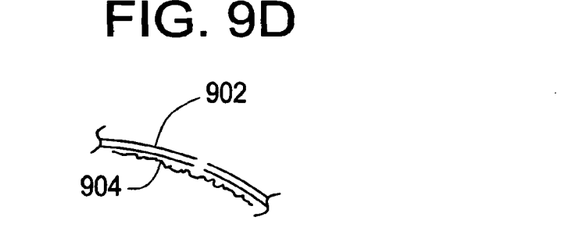
FIG. 9D is a partial cross-sectional view of a packaging system for packaging a gas-delivery device according to an embodiment of the present invention utilizing a self-sealing material.

Mechanisms for carrying out the removal of remaining gases (or a portion thereof) from the packaging may include devices such as a rubber septum or a self-sealing material provided for on a wall of the package. As shown in FIG. 9D, located on the interior (or between layers if multiple layers of material are used) the wall 902 of the package includes a self-sealing material 904. The self-sealing material allows a puncture through a wall of the package to self-seal, preferably after excess gas has escaped from the puncture. For example, after pressurization, and after a packaged device has absorbed a specified gas or gases (and may have also absorbed other therapeutic materials), the package is punctured and pressure is applied to the package to force out the remaining materials (e.g., gases and or therapeutic materials) which have not been absorbed by the device. After the package has decreased in size, the puncture device (e.g., a needle) may be removed and the force on the package is released. The puncture hole is then sealed from the flow of the self-sealing material. Alternatively, the package may be vented and re-sealed as shown in FIGS. 9A-9C. Specifically, as shown in FIG. 9A, a puncture device 906 may be used to puncture a wall 908 of the package which contains a gas delivery device 910. As shown, the ends 912 may be heat sealed.

FIG. 9B illustrates gas excess gas(es) escaping out of the puncture hole 914 (arrows B), which may be driven by pressure (arrows A) applied to the package. Thereafter, the end of the package may be heat sealed at a location of the puncture 914 which eliminates the puncture/vent from the final package.

Figure 9E:
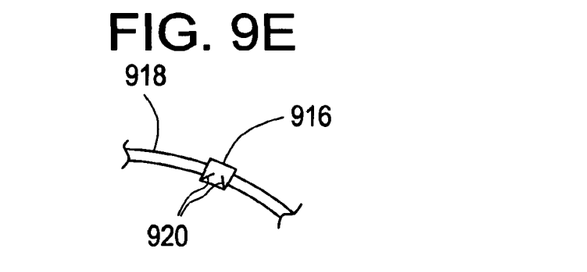
FIG. 9E is a partial cross-sectional view of a packaging system for packaging a gas-delivery device according to an embodiment of the present invention utilizing a valve type device.

Alternative to the above (or in addition thereto) the package may include a one-way valve 916 on a wall 918 of the package as shown in FIG. 9E. The valve may comprise one or more flaps 920 which allow one-way travel of gas—i.e., out of the package. Upon the device having absorbed the gas(es) and/or other therapeutic agents, pressure may be applied to the outside of the package which forces the valve 916 open and the excess agent out of the package.

Use of a Tissue Dressing System

Figure 5:
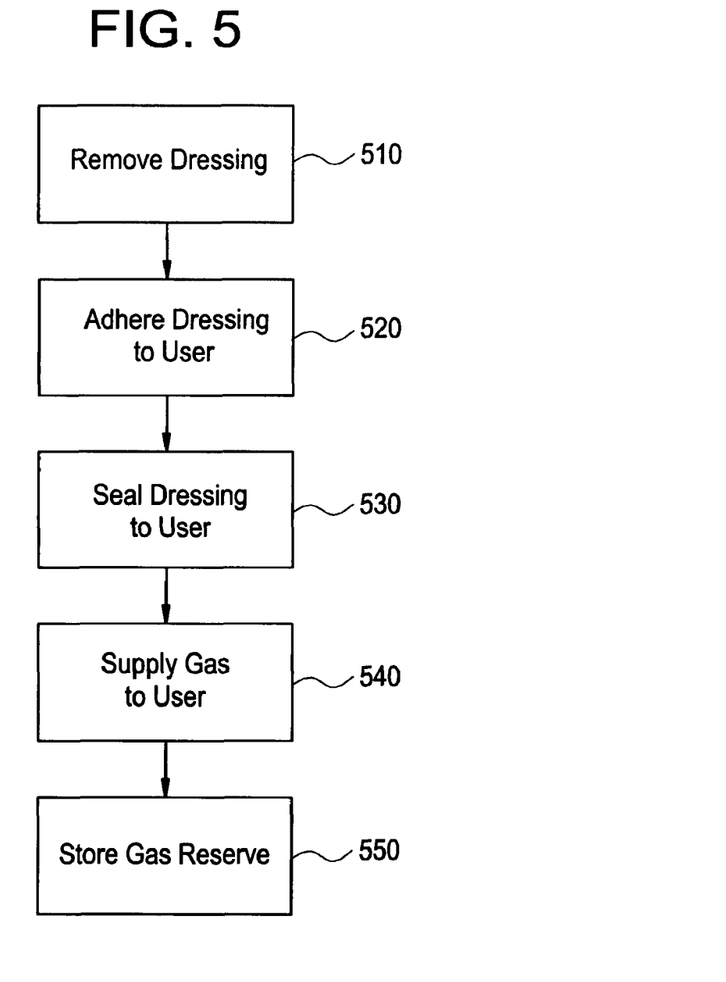
FIG. 5 illustrates a flow diagram for utilizing a dressing system according to one embodiment of the invention.

The flow diagram in FIG. 5 illustrates an exemplary process of utilizing the dressing system 100 according to one embodiment. Accordingly, in Block 510, the dressing system 100 is removed from a packaging.

In Block 520, the dressing system 100 is adhered to a user. In one embodiment, the dressing system 100 may cover a wound or broken skin of the user. In one embodiment, the dressing system 100 utilizes the adhesive backing 150 to adhere the dressing system 100 to the user.

In Block 530, a seal is formed between the dressing system 100 and the user. In one embodiment, the adhesive backing 150 forms the seal between the dressing system 100 and the user.

In Block 540, gas is supplied from the dressing system 100 to the user. In one embodiment, the permeable film 160 is positioned over the wound or broken skin of the user and allows the gas from the dressing system 100 to be supplied to wound of the user.

In another embodiment, the permeable film 160 may be positioned over intact skin of the user and allows the gas from the dressing system 100 to be supplied to the skin of the user. There are numerous practical applications in supplying oxygen to intact skin such as treating sun or radiation damaged skin, exfoliated skin, dermabraded skin, or providing nourishment to aged skin. There may be a synergistic effect with topical agents as well.

In Block 550, the gas within the reservoir 130 of the dressing system 100 may be stored until additional gas is supplied to the user through the permeable film 160.

Ophthalmologic Embodiments

Contact Lens Oxygenation. In another group of embodiments, a method and system for oxygenating or re-oxygenating contact lenses between uses is provided. Specifically, these embodiments include taking one or more contact lenses and placing them into a container that may be charged (and/or re-charged) with oxygen (or another specific gas or gases). Accordingly, users may then be able to oxygenate their own contact lenses. The lenses may be inserted into the case, for example, by popping them thru a gentle one way valve, or, alternatively, the lenses may be placed in a contact lens case and the case may then be oxygenated—either by inflating a collapsed case or flushing oxygen thru a rigid case (for example). The rigid case, accordingly, may include a venting mechanism for escaped gas.

Figure 10:
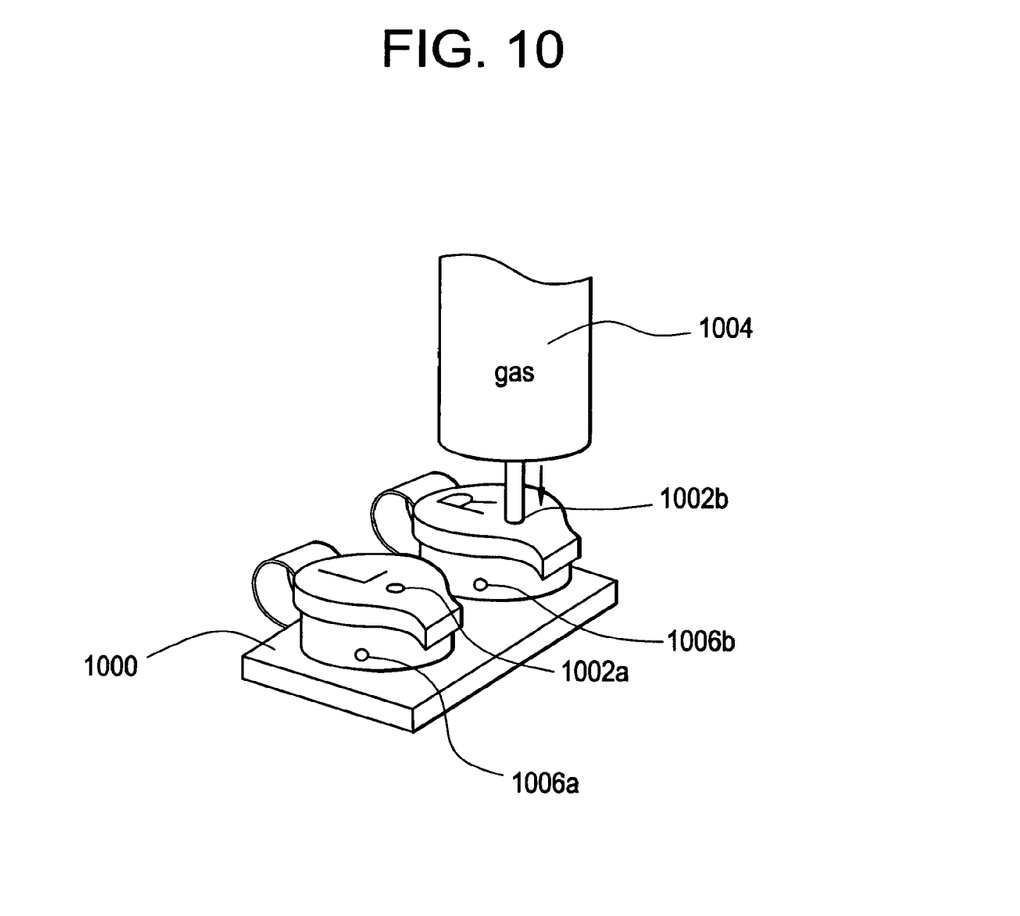
FIG. 10 is a perspective view of a contact-lens case capable of being charged with one or more predetermined gases, according to one embodiment of the present invention.

FIG. 10 illustrates an example of a contact lens case 1000 having a re-sealable port 1002a and 1002b, to which oxygen source 1004 can be flowed into. One-way valve vents 1006a and 1006b allows gases to flow out of each respective chamber of the contact lens case so as to insure fresh oxygen from oxygen source 1004 is contained in each chamber. These embodiments may, in addition to being used for contact lenses, also be used to oxygenate contacts that are used as "bandage lenses" after photorefractive keratectomy laser surgery for nearsightedness (for example). Keratectomy is a procedure where the outer cell layer of the cornea is removed, resulting in a wound that is a large abrasion on the eye, which is extremely painful to the patient. Accordingly, such bandage lenses are used as a protective covering on the cornea once anesthetic wears off.

Oxygen can be supplied a variety of ways to the contact lens case/container: e.g., via compressed oxygen stored in a cylinder or spray-can, or in prefilled, non-pressurized oxygen packages that allow the user to insert the device without leaking oxygen, and then open the package. Moreover, some embodiments of the invention may include contact-lens cases which include a reservoir of oxygen that, release oxygen to the area in which the contact lens is stored.

Other Embodiments

Still other embodiments of the invention include uses and methods for charging gas carrying media, such as oxygenating oxygen carrier gels, foams or solutions. For example, placing these materials into an impermeable package and filling the package with the predetermined gas, these materials become charged or saturated with gas while inside the package. Whether gases are supplied via a reservoir created between a barrier layer and a gas-permeable layer or through a gas-permeable continuous layer, the one or more gases may be stored in micro- or nano-reservoirs. These multiplicative reversible gas carrying reservoirs may include, for example, micro- or nano-particles, beads, spheres, mems (microelectro-mechanical systems), pigments or liposomes, for delivery to the target area. Further descriptions of such materials (e.g., repirocytes) can be found at:
www.foresight.org/Nanomedicine/Respirocytes.html, and www.foresight.org/Nanomedicine/
Respirocytes1.html#Sec22.

One form of respirocyte includes "molecular sorting rotors" which have been described by Drexler K E. *Nanosystems: Molecular Machinery, Manufacturing, and Computation*, New York: John Wiley & Sons, 1992. These tiny rotors have binding site "pockets" along their rims that are exposed alternately to the gas source to deliver or infuse gas from or into an interior microchamber. Once the binding site rotates to expose it to the interior chamber, the bound molecules are forcibly ejected by rods thrust outward by the cam surface. This can work equivalently in the reverse direction by ejecting gas after interior chamber has been charged with gas. These theoretical respirocytes can be designed to precisely take on and dispense oxygen and carbon dioxide separately or simultaneously under various conditions). Other reversible oxygen carriers include transport pigments which are conjugated proteins, or proteins complexed with another organic molecule or with one or more metal atoms. Transport pigments contain metal atoms such as $Cu^{2+}$ or $Fe^{3+}$. Besides hemoglobin and myoglobin, other natural oxygen carriers include hemocyanin, a blue copper-based pigment found in molluscs and crustaceans and chlorocruorin, a green iron-based pigment found in marine polychaete worms, and different oxides of vanadium. Other reversible oxygen-carriers include cobalt-based porphyrins such as coboglobin (a cobalt-based analog to hemoglobin) and cobaltodihistidine, and other metallic porphyrins, iron-indigo compounds, iridium complexes such as chloro-carbonyl-bis(triphenylphosphine)-iridium, a cobalt/ammonia complex described by (Hearon J Z, Burke D, Schade A L. Physicochemical studies of reversible and irreversible complexes of cobalt, histidine, and molecular oxygen. *J Natl Cancer Inst* 1949; 9:337-377), zeolite-bound divalent chromium, nonporphyrin lacunar iron complexes, and heme-linked NADPH oxidase.

Still other embodiments may include a device which includes a semi-solid, fluid or semi-fluid, gas infused material (i.e., gas being absorbed/adsorbed). Such semi-solid or semi-fluid products may include a gel, an ointment or a foam which is infused with one or more gases. Such materials may be cast on a film, and positioned over a wound or proximate a target where the desired gas(es) is to be provided. Such materials also may, as indicated above, be contained in a reservoir. Gel/foam materials may include but are not limited to hydrogels, acrylic resins, polyethylene glycols (or derivatives or cocktails thereof), polyacrylamide, glcosaminoglycan, polyethylene oxide, carboxymethyl-chitin hydrogel, poly(vinyl alcohol), nitric oxide releasing hydrogels, chitosan hydrogel, hydrogen peroxide gels, wound healing gels, bioerodible HEMA hydrogels, drug delivery gels (see for example Cox, Charles, "Treatment Options Gel With Innovative Drug Delivery Systems", Drug Delivery Technology (http://www-.drugdeliverytech.com/cgi-bin/articles.cgi?idArticle=55); Eisenbud, D et al., "Hydrogel Wound Dressings: where do we stand in 2003?", pp. 52-57, Ostomy Wound Manage, October 2003; Chiellini, Federica et al., "Bioerodible hydrogels based on 2-hydroxyethyl methacrylate: Synthesis and characterization", Journal of Applied Polymer Science, ISSN 0021-8995, Vol. 85, pp. 2729-2741 (2002). Each of the foregoing references is incorporated herein by reference in its entirety.

Materials infused with one or more predetermined gases, whether micro/nano particles or beads, gels, foams or combination thereof may also be bio-compatible and/or bio-resorbable materials. The term "bioresorbable materials" refers to a group of materials that have been shown to clinically resorb in living tissue (e.g., the human body), and include such products as sutures, dermal fillers and bone fillers (for example). According, such gas-delivery devices according to some embodiments of the present invention, when implanted into tissue (e.g., bone, cartilage, subdermal fat), biodegrade as they release (or when upon releasing a majority of) its stored gas such as oxygen or nitric oxide. Accordingly, such bioresorbable materials can include calcium phosphates, hydroxyapatite, apatites, calcium sulfates, bioresorbable polymers, collagen, gelatin, and bioactive glass. Calcium phosphates include alpha-tri-calcium phosphate and beta-tri-calcium phosphate.

Still other embodiments of the invention include uses and methods for storing and/or preserving oxygen media, tissue, and/or cells (e.g., red-blood cells), as well as uses and methods for oxygenating oxygen carrier solutions. Such solutions may include perfluorocarbons, polyhemoglobins, molecularly modified hemoglobin, and oxygenated Krebs solution.

Still other embodiments of the invention include methods to oxygenate scaffolds, tissues, artificial skin that may contain fibrinogen, collagen, hemoglobin, myoglobin, or other reversible oxygen binding agents for use as wound or aesthetic dressings. By placing these materials into a package and filling the package with oxygen, these materials become saturated with oxygen within the package and then upon application to the tissue, release that oxygen over time depending on the design and local oxygen demand.

The foregoing descriptions of specific embodiments of the invention have been presented for purposes of illustration and description. They are not intended to be exhaustive or to limit the invention to the precise embodiments disclosed, and naturally many modifications and variations are possible in light of the above teaching. The embodiments were chosen and described in order to explain the principles of the invention and its practical application, to thereby enable others skilled in the art to best utilize the invention and various embodiments with various modifications as are suited to the particular use contemplated.

What is claimed:

1. A gas delivery tissue dressing system for supplying one or more predetermined gases to a target environment, comprising;
    a top layer of non-permeable material;
    a reservoir;
    a bottom layer of permeable film providing control of gas diffusion in and out of the reservoir;
    a first seal sealing the top and bottom layers along an outer perimeter where the top and bottom layers meet; and
    packaging made from non-permeable material;
    wherein the reservoir is formed by the sealing of the top and bottom layers, the reservoir holding a volume of one or more first predetermined gases at concentrations at ambient levels and the package is hermetically sealed forming an internal volume receiving the entire reservoir, the packaging is charged with the one or more second predetermined gases above ambient levels then hermetically sealed and the second predetermined gases diffuse into the reservoir via the bottom layer causing the first predetermined gases to reach a concentration level higher than the ambient level and wherein the system does not generate gas.

2. The system of claim 1, wherein the one or more first and second predetermined gases includes oxygen.

3. The system of claim 1, wherein the one or more first predetermined gases contained in the reservoir is controllably released through the bottom layer to a target environment after removal from the package.

4. The system of claim 1, wherein a compliant porous insert is contained within the reservoir preventing reservoir collapse while within the package.

5. The system of claim 1, wherein the bottom layer includes an adhesive covering on a side away from the reservoir for adhering the bottom layer to a wound site.

6. The method of claim 1, wherein a compliant porous insert is contained within the reservoir preventing reservoir collapse while within the package.

7. A method providing a tissue dressing system, comprising the steps of:

(a) providing a top layer of non-permeable material;

(b) providing a bottom layer of permeable material;

(c) creating a reservoir holding a volume of first predetermined gases at ambient levels by sealing an area of contact around a perimeter of the top layer and bottom layer;

(d) inserting the reservoir completely within an interior of a package made of a non-permeable material;

(e) charging the interior of the package with second predetermined gases at a concentration higher than ambient levels then hermetically sealing the package; and (f) increasing the first predetermined gases within the reservoir to a level above the ambient level by diffusion of the second predetermined gases into the reservoir.

8. The method of claim 7, wherein the one or more first and second predetermined gases includes oxygen.

9. The method of claim 7 wherein the second predetermined gases originate from a gas-infused foam or gel within the package.

10. The method of claim 7, wherein the one or more first predetermined gases contained in the reservoir is controllably released through the bottom layer to a target environment after removal from the package.

11. The method of claim 10, wherein the bottom layer includes an adhesive covering a side away from the reservoir for adhering to a wound site.

\* \* \* \* \*